United States Patent
Secrest et al.

(10) Patent No.: US 10,772,648 B2
(45) Date of Patent: *Sep. 15, 2020

(54) RETRIEVAL DEVICE

(71) Applicant: UNITED STATES ENDOSCOPY GROUP, INC., Mentor, OH (US)

(72) Inventors: Dean J. Secrest, Concord, OH (US); Marlin E. Younker, Lantana, FL (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 59 days.

This patent is subject to a terminal disclaimer.

(21) Appl. No.: 15/676,725

(22) Filed: Aug. 14, 2017

(65) Prior Publication Data

US 2018/0055522 A1     Mar. 1, 2018

Related U.S. Application Data

(60) Continuation of application No. 15/344,915, filed on Nov. 7, 2016, now Pat. No. 9,730,716, which is a
(Continued)

(51) Int. Cl.
*A61B 17/221* (2006.01)
*A61B 17/00* (2006.01)

(52) U.S. Cl.
CPC ...... *A61B 17/221* (2013.01); *A61B 17/00234* (2013.01); *A61B 2017/00287* (2013.01); *A61B 2017/2212* (2013.01)

(58) Field of Classification Search
CPC ............ A61B 17/32056; A61B 17/221; A61B 2017/2212; A61B 2017/00287
See application file for complete search history.

(56) References Cited

U.S. PATENT DOCUMENTS

460,940 A    10/1891 Baughli
2,197,921 A   4/1940 Brown
(Continued)

FOREIGN PATENT DOCUMENTS

DE    19938902 A1    4/2000
EP     0446020 A1    9/1991
(Continued)

OTHER PUBLICATIONS

International Search Report and Written Opinion from PCT/US18/13005 dated Mar. 29, 2018.
(Continued)

*Primary Examiner* — Kathleen S Holwerda
(74) *Attorney, Agent, or Firm* — Calfee, Halter & Griswold LLP

(57) ABSTRACT

An endoscopic surgical device for retrieving severed tissue or foreign bodies from within a subject is disclosed. The device comprises a support unit and a tissue retrieving net system. The net system is carried by the support unit and may be inserted into the subject through an orifice or small incision and operated to retrieve tissue that has been severed by a conventional method. The net system comprises a net, a net actuator, a net deployment and retrieval assembly for transmitting motion between the net and its actuator. The net system further comprises at least one net connector disposed such that only one connector is within an articulation zone, defined by locations of severe bending of the device during operation.

9 Claims, 2 Drawing Sheets

Related U.S. Application Data continuation of application No. 10/965,542, filed on Oct. 14, 2004, now Pat. No. 9,486,188, which is a division of application No. 10/146,273, filed on May 15, 2002, now Pat. No. 6,814,739.

(60) Provisional application No. 60/292,168, filed on May 18, 2001.

(56) References Cited

U.S. PATENT DOCUMENTS

| | | |
|---|---|---|
| 2,626,447 A | 1/1953 | Hunt |
| 3,805,791 A | 4/1974 | Seuberth et al. |
| 4,083,706 A | 4/1978 | Wiley |
| 4,146,019 A | 3/1979 | Bass et al. |
| 4,200,104 A | 4/1980 | Harris |
| 4,202,338 A | 5/1980 | Bitrolf |
| 4,256,113 A | 3/1981 | Chamness |
| 4,311,143 A | 1/1982 | Komlya |
| 4,493,320 A | 1/1985 | Treat |
| 4,905,691 A | 3/1990 | Rydell |
| 4,966,589 A | 10/1990 | Kaufman |
| 5,009,642 A | 4/1991 | Sahi |
| 5,057,114 A | 10/1991 | Wittich et al. |
| 5,059,199 A | 10/1991 | Okada et al. |
| 5,078,716 A | 1/1992 | Doll |
| 5,084,054 A | 1/1992 | Bencini et al. |
| 5,098,441 A | 3/1992 | Wechler |
| 5,122,147 A | 6/1992 | Sewell, Jr. |
| 5,123,906 A | 6/1992 | Kelman |
| 5,147,371 A | 9/1992 | Washington |
| 5,156,590 A | 10/1992 | Vilmar |
| 5,171,233 A | 12/1992 | Amplatz et al. |
| 5,190,542 A | 3/1993 | Nakao |
| 5,192,280 A | 3/1993 | Parins |
| 5,192,286 A | 3/1993 | Phan et al. |
| 5,201,740 A | 4/1993 | Nakao et al. |
| 5,207,686 A | 5/1993 | Dolgin |
| 5,279,548 A | 1/1994 | Essig et al. |
| 5,336,227 A | 8/1994 | Nakao et al. |
| 5,354,303 A | 10/1994 | Spaeth et al. |
| 5,373,854 A | 12/1994 | Kolozsi |
| 5,374,273 A | 12/1994 | Nakao et al. |
| 5,376,094 A | 12/1994 | Kline |
| 5,417,697 A | 5/1995 | Wilk et al. |
| 5,423,830 A | 6/1995 | Schneebaum et al. |
| 5,441,503 A | 8/1995 | Considine et al. |
| 5,449,372 A | 9/1995 | Schmaitz et al. |
| 5,480,404 A | 1/1996 | Kammerer et al. |
| 5,496,330 A | 3/1996 | Bates et al. |
| 5,501,692 A | 3/1996 | Riza |
| 5,536,248 A | 7/1996 | Weaver et al. |
| 5,542,948 A | 8/1996 | Weaver et al. |
| 5,599,299 A | 2/1997 | Weaver et al. |
| 5,599,300 A | 2/1997 | Weaver et al. |
| 5,643,283 A | 7/1997 | Younker |
| 5,666,970 A | 9/1997 | Smith |
| 5,741,271 A | 4/1998 | Nakao et al. |
| 5,759,187 A | 6/1998 | Nakao et al. |
| 5,779,686 A | 7/1998 | Sato et al. |
| 5,782,840 A | 7/1998 | Nakao et al. |
| 5,785,689 A | 7/1998 | de Toledo |
| 5,788,681 A | 8/1998 | Weaver et al. |
| 5,810,776 A | 9/1998 | Bacich et al. |
| 5,843,028 A | 12/1998 | Weaver et al. |
| 5,843,051 A | 12/1998 | Adams et al. |
| 5,846,248 A | 12/1998 | Chu et al. |
| 5,860,987 A | 1/1999 | Ratcliff et al. |
| 5,906,594 A | 5/1999 | Scarfone et al. |
| 5,906,621 A | 5/1999 | Secrest et al. |
| 5,947,979 A | 9/1999 | Ouchi et al. |
| 5,961,526 A | 10/1999 | Chu et al. |
| 5,964,740 A | 10/1999 | Ouchi et al. |
| 5,971,994 A | 10/1999 | Fritzsch |
| 5,971,995 A | 10/1999 | Rousseau |
| 5,976,073 A | 11/1999 | Ouchi |
| 5,989,264 A | 11/1999 | Wright |
| 5,997,547 A | 12/1999 | Nakao et al. |
| 6,007,546 A | 12/1999 | Snow et al. |
| 6,010,512 A | 1/2000 | Chu et al. |
| 6,015,391 A | 1/2000 | Rishton et al. |
| 6,015,415 A | 1/2000 | Avellanet |
| 6,050,995 A | 4/2000 | Durgin |
| 6,068,603 A | 5/2000 | Suzuki |
| 6,093,195 A | 7/2000 | Ouchi |
| 6,123,665 A | 9/2000 | Kawano |
| 6,142,956 A | 11/2000 | Kortenbach et al. |
| 6,171,315 B1 | 1/2001 | Chu et al. |
| 6,174,291 B1 | 1/2001 | McMahon et al. |
| 6,183,482 B1 | 2/2001 | Bates et al. |
| 6,190,353 B1 | 2/2001 | Makower et al. |
| 6,193,672 B1 | 2/2001 | Clement |
| 6,210,416 B1 | 4/2001 | Chu et al. |
| 6,224,611 B1 | 5/2001 | Ouchi |
| 6,235,026 B1 | 5/2001 | Smith |
| 6,264,664 B1 | 7/2001 | Avellanet |
| 6,299,612 B1 | 10/2001 | Ouchi |
| 6,315,782 B1 | 11/2001 | Chu et al. |
| 6,319,260 B1 | 11/2001 | Yamamoto |
| 6,352,503 B1 | 3/2002 | Matsui et al. |
| 6,375,661 B2 | 4/2002 | Chu et al. |
| 6,383,194 B1 | 5/2002 | Pothula |
| 6,383,198 B1 | 5/2002 | Hamilton |
| 6,407,333 B1 | 6/2002 | Schroen |
| 6,409,733 B1 | 6/2002 | Conlon et al. |
| 6,440,138 B1 | 8/2002 | Reiley et al. |
| 6,458,074 B1 | 10/2002 | Matsui et al. |
| 6,500,182 B2 | 12/2002 | Foster |
| 6,517,551 B1 | 2/2003 | Driskill |
| 6,527,753 B2 | 3/2003 | Sekine et al. |
| 6,527,781 B2 | 3/2003 | Bates et al. |
| 6,602,262 B2 | 8/2003 | Griego et al. |
| 6,616,654 B2 | 9/2003 | McIennauer |
| 6,616,659 B1 | 9/2003 | de la Torre et al. |
| 6,669,716 B1 | 12/2003 | Gilson et al. |
| 6,685,722 B1 | 2/2004 | Rosenbluth et al. |
| 6,730,097 B2 | 5/2004 | Dennis |
| 6,743,228 B2 | 6/2004 | Lee et al. |
| 6,770,066 B1 | 8/2004 | Weaver et al. |
| 6,773,432 B1 | 8/2004 | Clayman et al. |
| 6,814,739 B2 | 11/2004 | Secrest |
| 6,827,710 B1 | 12/2004 | Money et al. |
| 6,945,956 B2 | 9/2005 | Waldhauser et al. |
| 7,001,354 B2 | 2/2006 | Suzuki et al. |
| 7,037,291 B2 | 5/2006 | Lee et al. |
| 7,037,307 B2 | 5/2006 | Dennis |
| 7,041,116 B2 | 5/2006 | Goto et al. |
| 7,044,947 B2 | 5/2006 | de la Torre et al. |
| 7,104,990 B2 | 9/2006 | Jenkins et al. |
| 7,122,003 B2 | 10/2006 | Nakao |
| 7,147,635 B2 | 12/2006 | Ciarrocca |
| 7,270,663 B2 | 9/2007 | Nakao |
| 7,387,632 B2 | 6/2008 | Ouchi |
| 7,547,310 B2 | 6/2009 | Whitfield |
| 7,575,585 B2 | 8/2009 | Goto et al. |
| 7,632,294 B2 | 12/2009 | Milbodker et al. |
| 7,691,110 B2 | 4/2010 | Secrest et al. |
| 7,704,249 B2 | 4/2010 | Woloszko et al. |
| 7,758,591 B2 | 7/2010 | Griego et al. |
| 7,785,250 B2 | 8/2010 | Nakao |
| 7,951,073 B2 | 5/2011 | Freed |
| 7,972,265 B1 | 7/2011 | Chin et al. |
| 8,016,838 B2 | 9/2011 | Kaye |
| 8,057,484 B2 | 11/2011 | Secrest |
| 8,066,689 B2 | 11/2011 | Mitelberg et al. |
| 8,070,756 B2 | 12/2011 | Secrest |
| 8,075,572 B2 | 12/2011 | Stefanchik et al. |
| 8,100,905 B2 | 1/2012 | Weitzner |
| 8,114,099 B2 | 2/2012 | Shipp |
| 8,128,592 B2 | 3/2012 | Mitelberg et al. |
| 8,167,893 B2 | 5/2012 | Motosugi |
| 8,187,266 B2 | 5/2012 | Dickens et al. |
| 8,216,272 B2 | 7/2012 | Shipp |
| 8,241,210 B2 | 8/2012 | Lunsford et al. |

(56) References Cited

U.S. PATENT DOCUMENTS

| | | |
|---|---|---|
| 8,267,933 B2 | 9/2012 | Hamou |
| 8,282,658 B2 | 10/2012 | Knapp et al. |
| 8,298,243 B2 | 10/2012 | Carlton et al. |
| 8,317,771 B2 | 11/2012 | Mitelberg et al. |
| 8,328,803 B2 | 12/2012 | Regadas |
| 8,343,168 B2 | 1/2013 | Kaye et al. |
| 8,357,148 B2 | 1/2013 | Boulais et al. |
| 8,366,612 B2 | 2/2013 | Rosenthal |
| 8,372,066 B2 | 2/2013 | Manwaring et al. |
| 8,388,630 B2 | 3/2013 | Teague et al. |
| 8,591,521 B2 | 11/2013 | Cherry et al. |
| 9,486,188 B2 * | 11/2016 | Secrest ............ A61B 17/00234 |
| 9,572,591 B2 | 2/2017 | Haack |
| 9,730,716 B2 * | 8/2017 | Secrest ............ A61B 17/00234 |
| 9,872,700 B2 | 1/2018 | Haack |
| 2002/0049423 A1 | 4/2002 | Howell et al. |
| 2002/0091394 A1 | 7/2002 | Reynolds et al. |
| 2002/0151889 A1 | 10/2002 | Swanson et al. |
| 2003/0004538 A1 | 1/2003 | Secrest et al. |
| 2003/0139750 A1 | 7/2003 | Shinozuka et al. |
| 2003/0195470 A1 | 10/2003 | Ponzi |
| 2003/0195492 A1 | 10/2003 | Gobron et al. |
| 2003/0216753 A1 | 11/2003 | Nishtala et al. |
| 2003/0236519 A1 | 12/2003 | Kear |
| 2004/0059352 A1 | 3/2004 | Burbank et al. |
| 2004/0092953 A1 | 5/2004 | Salameth |
| 2004/0158127 A1 | 8/2004 | Okada |
| 2005/0043743 A1 | 2/2005 | Dennis |
| 2005/0085808 A1 | 4/2005 | Nakao |
| 2005/0107668 A1 | 5/2005 | Smith |
| 2005/0165412 A1 | 7/2005 | Secrest et al. |
| 2005/0267489 A1 | 12/2005 | Secrest et al. |
| 2005/0267490 A1 | 12/2005 | Secrest et al. |
| 2006/0009759 A1 | 1/2006 | Christian et al. |
| 2006/0058776 A1 | 3/2006 | Bilsbury |
| 2006/0229640 A1 | 10/2006 | Whitfield |
| 2006/0235433 A1 | 10/2006 | Secrest |
| 2006/0247662 A1 | 11/2006 | Schwartz et al. |
| 2006/0264977 A1 | 11/2006 | Dana et al. |
| 2007/0016224 A1 | 1/2007 | Nakao |
| 2007/0016225 A1 | 1/2007 | Nakao |
| 2007/0250070 A1 | 10/2007 | Nobis et al. |
| 2007/0288035 A1 | 12/2007 | Okada |
| 2008/0045945 A1 | 2/2008 | Hamou |
| 2008/0183184 A1 | 7/2008 | Kaye et al. |
| 2008/0306336 A1 | 12/2008 | Kaye et al. |
| 2009/0043317 A1 | 2/2009 | Cavanaugh et al. |
| 2009/0112244 A1 | 4/2009 | Freudenthal |
| 2010/0036375 A1 | 2/2010 | Regadas |
| 2010/0268206 A1 | 10/2010 | Manwaring et al. |
| 2010/0268216 A1 | 10/2010 | Manwaring |
| 2011/0106077 A1 | 5/2011 | Yanuma et al. |
| 2011/0106107 A1 | 5/2011 | Binmoeller et al. |
| 2012/0004666 A1 | 1/2012 | Cowley et al. |
| 2012/0046667 A1 | 2/2012 | Cherry |
| 2012/0172662 A1 | 7/2012 | Kappel et al. |
| 2012/0172864 A1 | 7/2012 | Farin et al. |
| 2012/0184967 A1 | 7/2012 | Saleh |
| 2012/0283723 A1 | 11/2012 | Jenkins et al. |
| 2013/0018384 A1 | 1/2013 | Kappel et al. |
| 2013/0018385 A1 | 1/2013 | Keene et al. |
| 2014/0243885 A1 | 8/2014 | Eckhouse et al. |
| 2014/0276810 A1 | 9/2014 | Raybin |
| 2014/0276911 A1 | 9/2014 | Smith et al. |
| 2015/0105789 A1 | 4/2015 | Raybin et al. |
| 2015/0157345 A1 | 6/2015 | Haack et al. |
| 2016/0045210 A1 | 2/2016 | Cherry et al. |
| 2016/0242804 A1 | 8/2016 | Fleury |
| 2017/0007277 A1 | 1/2017 | Drapeau |
| 2017/0049471 A1 | 2/2017 | Gaffney |
| 2017/0231647 A1 | 8/2017 | Saunders |
| 2018/0028220 A1 | 2/2018 | Smith et al. |

FOREIGN PATENT DOCUMENTS

| | | |
|---|---|---|
| EP | 463363 A2 | 1/1992 |
| EP | 758551 A1 | 2/1997 |
| EP | 1180349 A1 | 2/2002 |
| EP | 1870015 A1 | 12/2007 |
| JP | 3-54652 | 5/1991 |
| JP | 5-091686 | 4/1993 |
| JP | 3250621 | 8/1993 |
| JP | H06154161 A | 6/1994 |
| JP | H07101802 A | 4/1995 |
| JP | 10-071166 | 3/1998 |
| JP | 10-174688 | 6/1998 |
| JP | 11-047154 | 2/1999 |
| JP | 11-226024 | 8/1999 |
| JP | H11309150 A | 11/1999 |
| JP | 2000-175930 | 6/2000 |
| JP | 2000-210295 | 8/2000 |
| JP | 2000-316868 | 11/2000 |
| JP | 2000-342600 | 12/2000 |
| JP | 2003-052707 | 2/2003 |
| JP | 2003-511140 | 3/2003 |
| JP | 2004-532683 A | 10/2004 |
| JP | 2007-534451 | 11/2007 |
| WO | 93/015671 A1 | 8/1993 |
| WO | 99/42041 A1 | 8/1999 |
| WO | 99/51159 A1 | 10/1999 |
| WO | 02/094082 A2 | 11/2002 |
| WO | 03/105674 A2 | 12/2003 |
| WO | 05/115116 A2 | 12/2005 |
| WO | 05/115120 A2 | 12/2005 |
| WO | 2006112231 A1 | 10/2006 |
| WO | 2007000452 A2 | 1/2007 |
| WO | 08/094931 A2 | 8/2008 |
| WO | 08/154406 A2 | 12/2008 |

OTHER PUBLICATIONS

International Search Report and Written Opinion from PCT/US18/13017 dated Apr. 6, 2018.
Office Action from U.S. Appl. No. 11/137,814 dated Feb. 12, 2009.
Office Action from U.S. Appl. No. 14/875,028 dated Mar. 29, 2018.
Response to Office Action from U.S. Appl. No. 14/875,028 dated Jun. 19, 2018.
Office Action from U.S. Appl. No. 14/875,028 dated Aug. 27, 2018.
Response to Office Action from U.S. Appl. No. 14/875,028 dated Nov. 27, 2018.
Office Action from U.S. Appl. No. 15/401,545 dated Aug. 2, 2018.
Response to Office Action from U.S. Appl. No. 15/401,545 dated Oct. 30, 2018.
Communication Pursuant to Article 94(3) EPC from European Application No. 05755966.8 dated Oct. 22, 2018.
Communication Pursuant to Artile 94(3) EPC from European Application No. 12162767.3 dated Nov. 12, 2018.
English Translation of Office Action from Japanese Patent Application No. 2016-0540331 dated May 29, 2018.
Extended Search Report from European Application No. 18167984.6 dated Jul. 30, 2018.
Response to Office Action from U.S. Appl. No. 15/425,228 dated Aug. 31, 2017.
Extended Search Report from European Application No. 14841802.3 dated Jan. 30, 2017.
English Translation of Office Action from Japanese Patent Application No. 2016-052687 dated Jan. 31, 2017.
Response to Office Action from U.S. Appl. No. 14/875,028 dated Jan. 17, 2018.
Office Action from U.S. Appl. No. 14/875,028 dated Dec. 26, 2018.
Office Action from U.S. Appl. No. 15/401,545 dated Mar. 8, 2019.
Office Action from European Application No. 0279222.6 dated Sep. 23, 2010.
Response from European Application No. 02729222.6 dated Jan. 28, 2011.
Office Action from European Application No. 02729222.6 dated Sep. 7, 2011.

(56) References Cited

OTHER PUBLICATIONS

Response from European Application No. 02729222.6 dated Jan. 10, 2012.
Search Report from European Application No. 05757183.8 dated Oct. 4, 2012.
Office Action from European Application No. 05757183.8 dated Feb. 11, 2013.
Response from European Application No. 05757183.8 dated Aug. 19, 2013.
Search Report from European Application No. 05755966.8 dated Jun. 5, 2012.
Office Action from European Application No. 05755966.8 dated Sep. 27, 2012.
Response from European Application No. 05755966.8 dated Apr. 5, 2013.
Search Report from European Application No. 06112733.8 dated Jan. 12, 2007.
Response from European Application No. 05112733.8 dated Jan. 7, 2009.
Office Action from European Application No. 06112733.8 dated Feb. 19, 2009.
Search Report from European Application No. 12162767.3 dated Dec. 23, 2015.
Office Action from Japanese Application No. 2007-511105 dated Sep. 3, 2009.
Response from Japanese Application No. 2007-511105 dated Mar. 5, 2010 along with English translation of claims and relevant portion of remarks made in Amendment.
Office Action from Japanese Application No. 2007-515282 dated Jan. 7, 2011.
Response from Japanese Application No. 2007-515282 dated Apr. 7, 2011 along with English translation of claims and relevant portion of remarks made in Amendment.
Office Action from Japanese Application No. 2007-515282 dated Jul. 27, 2011.
Response from Japanese Application No. 2007-515282 dated Mar. 5, 2012 along with relevant portion of remarks made in Amendment.
Office Action from Japanese Application No. 2009-548397 dated Sep. 28, 2012.
Response from Japanese Application No. 2009-548397 dated Mar. 28, 2013 along with English translation of claims and relevant portion of remarks made in Amendment.
Office Action from Japanese Application No. 2010-511374 dated Dec. 28, 2012.
Response from Japanese Application No. 2010-511374 dated Jul. 5, 2013 along with English translation of claims and relevant portion of remarks made in Amendment.
Advanced Lin Retrieval Devices Brochure, issued by US Endoscopy 760204, Rev. A, dated at least as early as the filing date of the subject application.
Cook Medical brochure pages, Esophageal/Gastric Colonic: Snares, 3 pgs., date is at least as early as Jul. 1, 2013.
Juan-Marie et al. Double-Lumen Snare Injector: Introducing the Double-Lumen Concept in Ancillary Pollypectomy Equipment, Gastrointestinal Endoscopy, vol. 57, No. 5, 2003.
MTW Endoskopie, brochure, one page, date is at least as early as Jul. 1, 2013.
Olympus, EndoTherapy, Polypectomy, brochure, 3 pgs., date is at least as early as Jul. 1, 2013.
English translation of Office Action in Japanese Application No. 2014-004359 dated Jan. 20, 2015.
Extended European Search Report in European Application No. 08756773.1 dated Feb. 23, 2015.
Office Action from U.S. Appl. No. 14/565,024 dated Dec. 9, 2015.
Office Action from European Application No. 05757183.8 dated Nov. 16, 2015.
Response to Office Action from European Application No. 05757183.8 dated Mar. 17, 2016.
Extended European Search Report in European Application No. 08714094.3 dated Jan. 27, 2016.
Response to Office Action from U.S. Appl. No. 14/016,906 dated Dec. 13, 2016.
Office Action from U.S. Appl. No. 14/016,906 dated Mar. 10, 2017.
Response to Office Action from U.S. Appl. No. 14/016,906 dated Aug. 10, 2017.
Notice of Allowance from U.S. Appl. No. 14/016,906 dated Sep. 27, 2017.
Office Action from U.S. Appl. No. 14/565,024 dated Jul. 5, 2016.
Notice of Allowance from U.S. Appl. No. 14/565,024 dated Aug. 30, 2016.
Office Action from U.S. Appl. No. 14/875,028 dated Jun. 1, 2017.
Response to Office Action from U.S. Appl. No. 14/875,028 dated Sep. 27, 2017.
Office Action from U.S. Appl. No. 14/875,028 dated Oct. 18, 2017.
Office Action from U.S. Appl. No. 15/344,915 dated Jan. 18, 2017.
Response Office Action from U.S. Appl. No. 15/344,915 dated Apr. 18, 2017.
Notice of Allowance from U.S. Appl. No. 15/344,915 dated Jun. 26, 2017.
Office Action from U.S. Appl. No. 15/425,228 dated Apr. 12, 2017.
Response to Office Action from U.S. Appl. No. 15/425,228 dated Jul. 10, 2017.
Office Action from U.S. Appl. No. 15/425,228 dated Aug. 23, 2017.
International Search Report and Written Opinion from PCT/US02/15465 dated Aug. 26, 2013.
International Preliminary Examination Report from PCT/US02/15465 dated Nov. 12, 2003.
International Search Report from PCT/US05/18294 dated May 25, 2005, 10 pgs.
International Search Report and Written Opinion from PCT/US05/18497 dated May 8, 2008.
International Search Report and Written Opinion from PCT/US08/52342 dated Jul. 30, 2008.
International Search Report and Written Opinion from PCT/US08/066161 dated Sep. 22, 2008.
International Search Report and Written Opinion from PCT/US2014/053828 dated Dec. 30, 2014.
International Preliminary Report on Patentability from PCT/US2014/053828 dated Mar. 8, 2016.
Office Action from U.S. Appl. No. 10/146,273 dated Oct. 22, 2003.
Response from U.S. Appl. No. 10/146,273 dated Jan. 16, 2004.
Office Action from U.S. Appl. No. 10/146,273 dated Apr. 14, 2004.
Response from U.S. Appl. No. 10/146,273 dated May 26, 2004.
Notice of Allowance from U.S. Appl. No. 10/146,273 dated Jul. 12, 2004.
Office Action from U.S. Appl. No. 10/965,542 dated Jun. 25, 2008.
Interview Summary from U.S. Appl. No. 10/965,542 dated Oct. 14, 2008.
Response from U.S. Appl. No. 10/965,542 dated Oct. 27, 2008.
Office Action from U.S. Appl. No. 10/965,542 dated Feb. 4, 2009.
Response from U.S. Appl. No. 10/965,542 dated Aug. 4, 2009.
Office Action from U.S. Appl. No. 10/965,542 dated Oct. 14, 2009.
Response from U.S. Appl. No. 10/965,542 dated Apr. 14, 2010.
Office Action from U.S. Appl. No. 10/965,542 dated Jun. 30, 2010.
Response from U.S. Appl. No. 10/965,542 dated Dec. 29, 2010.
Office Action from U.S. Appl. No. 10/965,542 dated May 21, 2013.
Response from U.S. Appl. No. 10/965,542 dated Sep. 23, 2013.
Office Action from U.S. Appl. No. 10/965,542 dated Dec. 27, 2013.
RCE and Response to Office Action from U.S. Appl. No. 10/965,542 dated May 27, 2014.
Office Action from U.S. Appl. No. 10/965,542 dated Aug. 11, 2014.
Interview Summary from U.S. Appl. No. 10/965,542 dated Dec. 17, 2014.
Amendment from U.S. Appl. No. 10/965,542 dated Jan. 12, 2015.
Office Action from U.S. Appl. No. 10/965,542 dated Feb. 20, 2015.
Response to Office Action from U.S. Appl. No. 10/965,542 dated Aug. 20, 2015.
Office Action from U.S. Appl. No. 10/965,542 dated Sep. 18, 2015.
Response to Office Action from U.S. Appl. No. 10/965,542 dated Jan. 19, 2016.
Notice of Allowance from U.S. Appl. No. 10/965,542 dated Jul. 11, 2016.
Office Action from U.S. Appl. No. 11/137,763 dated Jun. 24, 2009.

(56) References Cited

OTHER PUBLICATIONS

Supplemental Office Action from U.S. Appl. No. 11/137,763 dated Sep. 9, 2009.
Response from U.S. Appl. No. 11/137,763 dated Mar. 3, 2010.
Office Action from U.S. Appl. No. 11/137,763 dated May 25, 2010.
Response from U.S. Appl. No. 11/137,763 dated Jul. 23, 2010.
Advisory Action from U.S. Appl. No. 11/137,763 dated Aug. 5, 2010.
Office Action from U.S. Appl. No. 11/137,763 dated Dec. 23, 2010.
Interview Summary from U.S. Appl. No. 11/137,763 dated May 12, 2011.
Response from U.S. Appl. No. 11/137,763 dated May 23, 2011.
Office Action from U.S. Appl. No. 11/137,763 dated Aug. 4, 2011.
Response from U.S. Appl. No. 11/137,763 dated Aug. 22, 2011.
Notice of Allowance from U.S. Appl. No. 11/137,763 dated Sep. 19, 2011.
Office Action from U.S. Appl. No. 11/137,814 dated May 16, 2007.
Response from U.S. Appl. No. 11/137,814 dated Aug. 16, 2007.
Office Action from U.S. Appl. No. 11/137,814 dated Dec. 7, 2007.
Response from U.S. Appl. No. 11/137,814 dated Apr. 7, 2008.
Office Action from U.S. Appl. No. 11/137,814 dated Jul. 18, 2008.
Response from U.S. Appl. No. 11/137,814 dated Sep. 18, 2008.
Interview Summary and Advisory Action from U.S. Appl. No. 11/137,814 dated Oct. 14, 2008.
Response from U.S. Appl. No. 11/137,814 dated Nov. 18, 2008.
Response from U.S. Appl. No. 11/137,814 dated Aug. 12, 2009.
Office Action from U.S. Appl. No. 11/137,814 dated Nov. 23, 2009.
Response from U.S. Appl. No. 11/137,814 dated Jan. 19, 2010.
Notice of Allowance from U.S. Appl. No. 11/137,814 dated Feb. 18, 2010.
Office Action from U.S. Appl. No. 11/404,345 dated Jun. 27, 2008.
Interview Summary from U.S. Appl. No. 11/404,345 dated Oct. 7, 2008.
Response from U.S. Appl. No. 11/404,345 dated Nov. 26, 2008.
Office Action from U.S. Appl. No. 11/404,345 dated Mar. 11, 2010.
Response from U.S. Appl. No. 11/404,345 dated May 11, 2010.
Advisory Action from U.S. Appl. No. 11/404,345 dated May 27, 2010.
Response from U.S. Appl. No. 11/404,345 dated Sep. 13, 2010.
Office Action from U.S. Appl. No. 11/404,345 dated Dec. 29, 2010.
Response from U.S. Appl. No. 11/404,345 dated May 25, 2011.
Notice of Allowance from U.S. Appl. No. 11/404,345 dated Aug. 19, 2011.
Office Action from U.S. Appl. No. 12/021,903 dated Dec. 10, 2009.
Response from U.S. Appl. No. 12/021,903 dated Jun. 9, 2010.
Office Action from U.S. Appl. No. 12/021,903 dated Aug. 5, 2010.
Response from U.S. Appl. No. 12/021,903 dated Oct. 7, 2010.
Interview Summary from U.S. Appl. No. 12/021,903 dated Oct. 5, 2010.
Office Action from U.S. Appl. No. 12/021,903 dated Dec. 29, 2011.
Interview Summary from U.S. Appl. No. 12/021,903 dated Mar. 21, 2012.
Response from U.S. Appl. No. 12/021,903 dated May 25, 2012.
Notice of Allowance from U.S. Appl. No. 12/021,903 dated Aug. 9, 2012.
Notice of Allowance from U.S. Appl. No. 12/021,903 dated Nov. 20, 2012.
Office action from U.S. Appl. No. 12/135,473 dated Nov. 16, 2010.
Response from U.S. Appl. No. 12/135,473 dated Feb. 15, 2011.
Interview Summary from U.S. Appl. No. 12/135,473 dated Feb. 15, 2011.
Office Communication from U.S. Appl. No. 12/135,473 dated Apr. 15, 2011.
Notice of Allowance from U.S. Appl. No. 12/135,473 dated Jun. 27, 2011.
Office Action from U.S. Appl. No. 13/213,689 dated Dec. 20, 2012.
Response from U.S. Appl. No. 13/213,689 dated Mar. 18, 2013.
Notice of Allowance from U.S. Appl. No. 13/213,689 dated Jul. 23, 2013.
Office Action from U.S. Appl. No. 14/061,395 dated Jun. 18, 2015.
Response to Office Action from U.S. Appl. No. 14/061,395 dated Sep. 17, 2015.
Office Action from U.S. Appl. No. 14/016,906 dated Apr. 8, 2015.
Response to Office Action from U.S. Appl. No. 14/016,906 dated Feb. 12, 2016.
Office Action from U.S. Appl. No. 14/016,906 dated May 31, 2016.
Response to Office Action from U.S. Appl. No. 14/016,906 dated Jul. 28, 2016.
Office Action from U.S. Appl. No. 14/016,906 dated Sep. 13, 2016.
Office Action from U.S. Appl. No. 14/565,024 dated Apr. 17, 2015.
Response to Office Action from U.S. Appl. No. 14/565,024 dated Aug. 17, 2015.
Response to Office Action from U.S. Appl. No. 14/565,024 dated Mar. 25, 2016.
Advisory Action from U.S. Appl. No. 14/565,024 dated Apr. 14, 2016.
Amendment from U.S. Appl. No. 14/565,024 dated Jul. 28, 2016.
Supplemental European Search Report from European Application No. 02729222.6 dated Aug. 20, 2009.
Response from European Application No. 02729222.6 dated Nov. 17, 2009.
Response to Office Action from U.S. Appl. No. 14/875,028 dated Mar. 26, 2019.
Office Action from U.S. Appl. No. 14/875,028 dated Jul. 1, 2019.
Response to Office Action Office Action from U.S. Appl. No. 15/401,545 dated Jun. 10, 2019.
Office Action from U.S. Appl. No. 15/401,545 dated Jun. 27, 2019.
Response to Office Action Office Action from U.S. Appl. No. 15/401,545 dated Sep. 26, 2019.
Office Action from U.S. Appl. No. 15/676,725 dated Jul. 5, 2019.
Communication Pursuant to Article 94(3) from European Application No. 18167984.6 dated Jun. 6, 2019.
Notice of Allowance from U.S. Appl. No. 15/866,401 dated Mar. 18, 2020.
Response to Office Action from U.S. Appl. No. 15/676,725 dated Jan. 6, 2020.
Notice of Allowance from U.S. Appl. No. 15/401,545 dated Jan. 16, 2020.
Notice of Allowance from U.S. Appl. No. 15/866,401 dated Jan. 23, 2020.
Response to Office Action from U.S. Appl. No. 14/875,028 dated Jan. 2, 2020.
Office Action from U.S. Appl. No. 14/875,028 dated Apr. 16, 2020.
Notice of Allowance from U.S. Appl. 15/866,273 dated Apr. 22, 2020.
Notice of Allowance from U.S. Appl. 15/866,273 dated May 5, 2020.
Notice of Allowance from U.S. Appl. No. 15/866,273 dated Jun. 4, 2020.
Extended Search Report from European Application No. 18736126.6 dated Jul. 7, 2020.
Extended Search Report from European Application No. 20152855.1 dated Jun. 16, 2020.

* cited by examiner

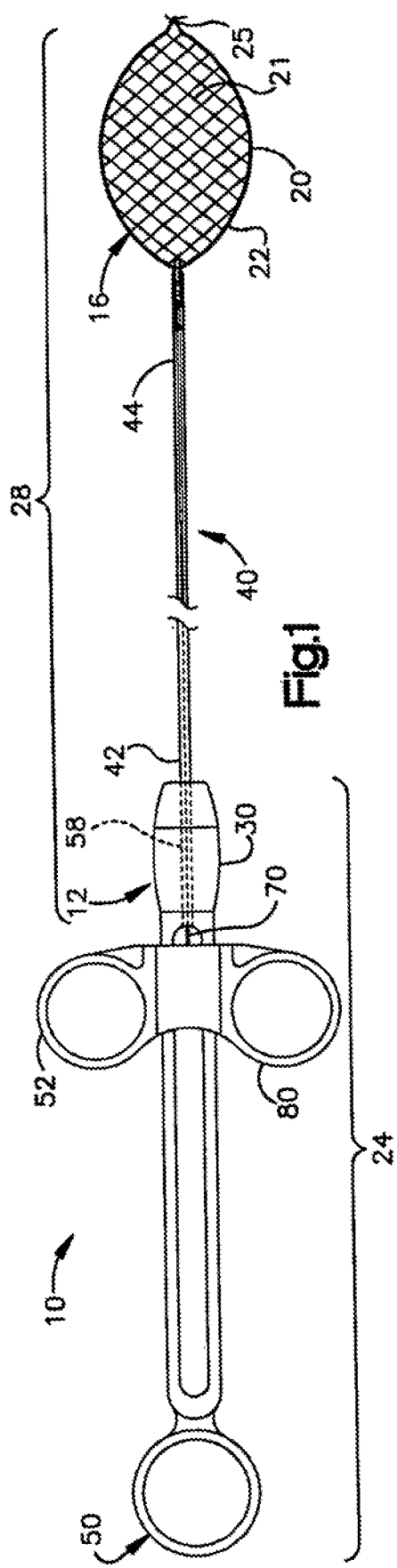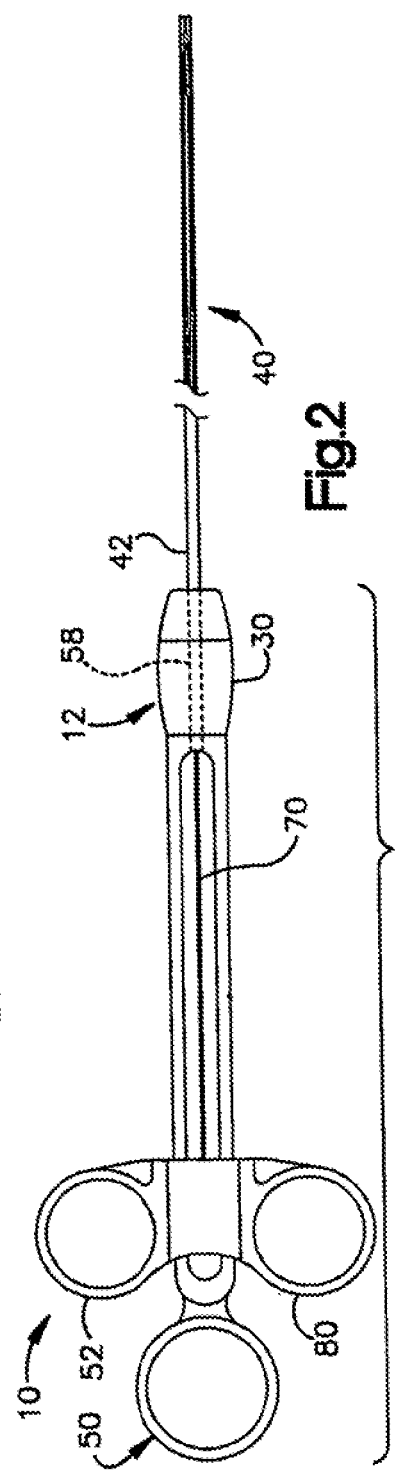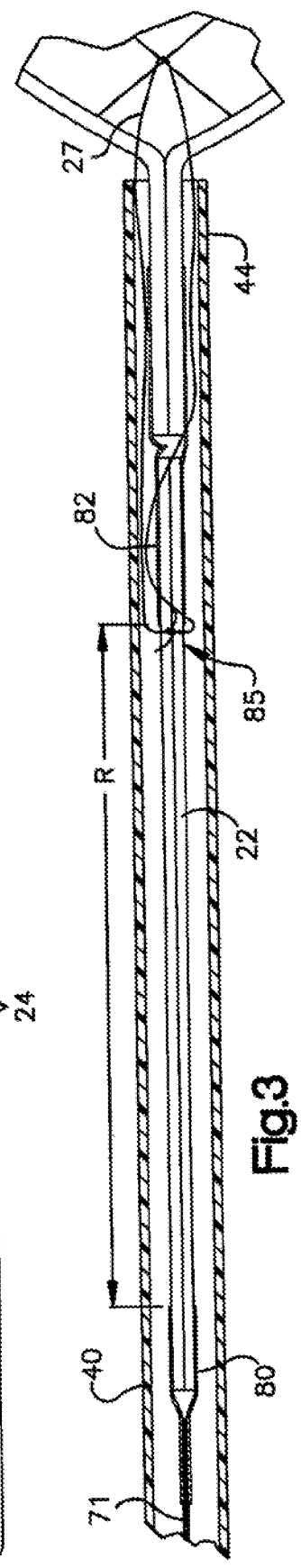

RETRIEVAL DEVICE

CROSS-REFERENCE TO RELATED APPLICATIONS

This application is a continuation of U.S. Non-Provisional Patent Application Ser. No. 15/344,915, entitled "Retrieval Device," filed Nov. 7, 2016, is a continuation of U.S. Non-Provisional patent application Ser. No. 10/965,542 entitled "Retrieval Device," filed Oct. 14, 2004, and issued as U.S. Pat. No. 9,486,188 on Nov. 8, 2016, which is a divisional of U.S. Non-Provisional patent application Ser. No. 10/146,273 filed May 15, 2002, and issued as U.S. Pat. No. 6,814,739 on Nov. 9, 2004, which claims benefit of U.S. Patent Provisional Application No. 60/292,168, entitled "Retrieval Device," filed on May 18, 2001, the entire disclosures of which are incorporated herein by reference.

FIELD OF THE INVENTION

The present invention relates to surgical devices and more particularly to endoscopic retrieval devices constructed for retrieving relatively small pieces of sample tissue or foreign bodies from a human subject through orifices or small incisions.

BACKGROUND OF THE INVENTION

Snares, baskets, and graspers are in widespread use for severing capturing and retrieving tissue specimens and foreign bodies from within subjects. The devices are used in human and animal subjects, in laparoscopic surgeries and other procedures where access within a subject is only possible via a small opening. One exemplary use is for cutting off and retrieving intestinal polyps where a wire snare, passed through an colonoscope instrument channel, encircles and is tightened about an intestinal polyp to sever the polyp. The severed polyp is retrieved in a net inserted through the instrument channel. The net is manipulated to enclose the polyp and then withdrawn with the instrument so that the tissue architecture remains undisturbed.

In this procedure, as well as others, the net and snare must be quite compact in order to pass into the subject through the instrument channel, or other passage. Prior art proposals have employed snares supported within plastic tubes that were snaked into the subject to locate the snare where desired. The snare was then deployed from its tube, manipulated to cut off the polyp and retrieved into the tube for removal from the subject.

A net, collapsed within another tube, was introduced through the instrument channel, etc., for removing the polyp. When near a target polyp, the net was deployed, like the snare, and manipulated to net the polyp. The net was then closed sufficiently to secure the polyp and withdrawn from the subject.

U.S. Pat. No. 5,643,283 to Younker, which is incorporated herein by reference in its entirety, discloses a device for retrieving an object from within a subject. The device comprises a shaft and a compressible pouch for receiving the object positioned adjacent a distal end of the shaft. The pouch includes a mouth which can be opened and closed. The pouch is retained, in proximity to the distal end of the shaft, on a cable loop by a slidable tether. The net is free to slide on the cable loop to form a pouch at the distal end of the shaft. The tether is fixed at a second location near the proximal end of the shaft, and in one embodiment, is tied off to a ring and secured with heat shrink tubing. When the targeted foreign object is within the pouch, a clinician disengages the ring portion of the handle to close the net around the object. The clinician then removes the device from the patient and unloads the object from the net. The clinician then places the ring on a post, in order to pack the pouch into the distal end of the shaft.

In operation of a commercial embodiment of U.S. Pat. No. 5,643,283, several problematic issues have surfaced. Clinicians have experienced difficulty in understanding the operation of the tether, in particular, the interaction of the ring and post. The ring is to be used to pull the net inside the shaft only when an object is not within the net. In preparation to capture an object, the ring should be disengaged to release the net. The net is then slid over the targeted object and the net is closed. At this point, proper operation would involve merely removing the device from the patient. However, some clinicians when operating the device try to further pull the net inside the shaft when the net is bundled up at distal end of cable loop. This will cause the net to jam, or in some cases, damages the tubing. The occasional improper operation of the device sometimes causes permanent malfunction.

The commercial embodiment discussed above also adds undesirable expense to the product. Specifically, the full length tether and heat shrink operation add material cost and labor assembly cost to the device.

The present invention provides a new and improved retrieval device that is so constructed and arranged that net movement during deployment and retrieval is not prohibitively restricted. Secure net attachment is assured and that provides for convenient net packing in the introducer passage. The device provides a convenient and economical method of sample retrieval during endoscopic procedures. The new retrieval device is easy assemble, manufactured at a reduced cost, and easier to use by the end consumer.

SUMMARY OF THE INVENTION

In one illustrated embodiment of the present invention an endoscopic surgical device for retrieving severed tissue from within a human subject is provided. The device includes a support unit and a tissue retrieving net system.

The support unit includes a body and an elongated introducer member. The body defines a first passage therethrough. The introducer has a first end section proximal and fixed with respect to the body and a second end section remote form the body. The introducer member further defines a second passage aligned with the first passage and opening at the second end section.

The tissue retrieving net system includes a net, a net deployment and retrieval assembly and a net actuator system.

The net includes a wire-like resilient loop and a net element having a mouth section slidably disposed on the loop and a tissue receiving pouch section. The loop terminates with two relatively parallel loop cables. The net is disposed adjacent the second end for deployment and retraction through the second passage opening.

The net deployment and retrieval assembly extends substantially through the first and second passages and connects to the net. The assembly further includes a motion transmitting member extending in the second passage to the loop.

The net actuator unit includes a first handle fixed with respect to the body and a second handle fixed with respect to the motion transmitting member and movable relative to the first handle. The act of shifting the second handle relative to the first handle shifts the net into and out of the second passage opening.

The introducer member second passage has a diameter substantially smaller than the width of the loop as deployed. The member engages the loop at the second end section opening and resiliently collapses and elongates the loop as the net is retracted and moves into the introducer member passage. The loop resiliently returns to its uncollapsed configuration as it is deployed.

In one embodiment, the net system includes at least one connector adapted to fasten each loop cable. The ends of the net element are secured to the motion transmitting member on the proximal side of the at least one connector with respect to the support unit.

In a second embodiment, the net system further includes a first connector, a second net connector proximal to the second passage opening, and an intermediate portion defined by an axial space on the loop cables between the first connector and the second connector. The first connector and the second connector are adapted to fasten each loop cable. Ends of the net, element are secured to the loop within the intermediate loop portion between the first connector and the second connector.

The deployment and retrieval assembly may include a thin, flexible wire-like motion transmitting member between the net actuator unit and the loop. The motion transmitting member extends within an introducer guide passage which closely surrounds the motion transmitting member and constrains the member for translational longitudinal motion within the passage.

The first connector may be disposed at least 6 inches from the second connector, such that only one connector is within an articulation zone during deployment of the net element.

The ends of the net element may be secured to the motion transmitting member adjacent a proximal shoulder of the connector with respect to the support unit.

The present invention offers advantages over devices available in the prior art. In a second embodiment, the net is fixed distally and proximally by the use of a first and second connector. The connectors are sufficiently spaced apart to provide secure net attachment without the use of additional tether mechanisms. The connectors are positioned such that only one may be within an articulation zone of the endoscope at a time, permitting ease of net deployment in a variety of geometric operating configurations.

In a first embodiment, only one connector is used to secure the proximal side of the net. This technique decreases the amount of cable loop length within the articulation zone. The reduction in cable loop length effectively reduces the amount of rigid material within the articulation zone of the endoscope at a time, further permitting ease of net deployment in a variety of geometric operating configurations.

The device is also easier to assemble and less expensive to manufacture than certain conventional designs.

Further features and advantages of the invention will become apparent from the following detailed description made with reference to the accompanying drawings.

BRIEF DESCRIPTION OF THE DRAWINGS

FIG. 1 is an elevational view of a surgical device constructed according to one embodiment of the present invention, illustrated with the net element deployed;

FIG. 2 is a view similar to FIG. 1, illustrated with the net element retracted;

FIG. 3 is an enlarged fragmentary view of a part of the device illustrated in FIG. 1, showing detail of the introducer member.

BEST MODE CONTEMPLATED FOR CARRYING OUT THE INVENTION

Figure 4:
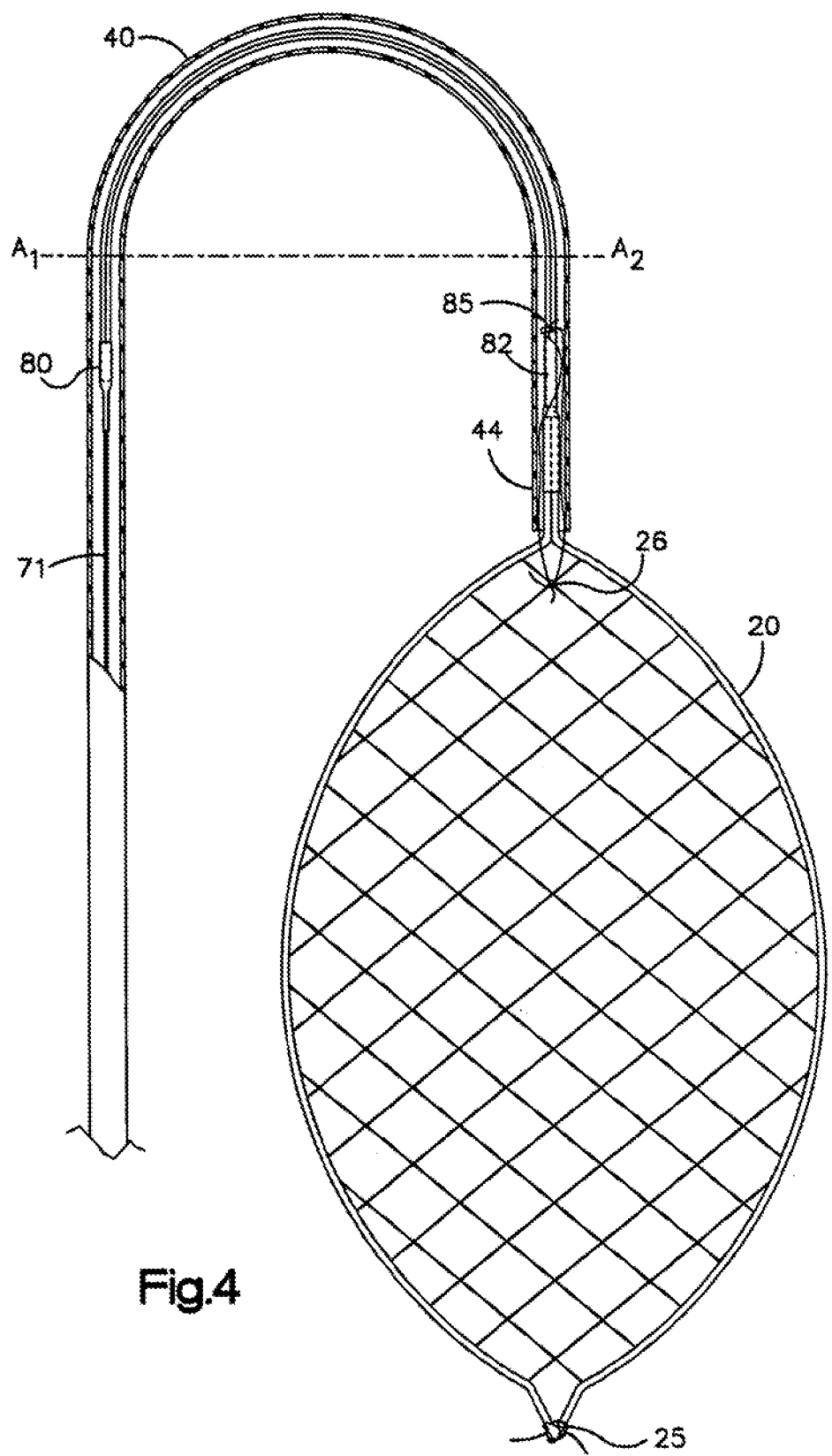
FIG. 4 is an enlarged fragmentary view of part of the device illustrated in FIG. 1, with the device show as positioned in a sample configuration within a subject.

An endoscopic surgical device 10 for retrieving severed tissue and or foreign bodies from within a subject is illustrated by the drawings. Referring to FIGS. 1 and 2, in one embodiment, the device 10 comprises a support u nit 12 and a tissue retrieving net system 16. The net system is carried by the unit 12 and is so constructed and arranged that it may be inserted into the subject through an orifice or small incision and operated to retrieve a tissue sample previously detached from the subject by a conventional method, e.g., a snare/cautery system. Accordingly, the net system 16 comprises a net 20, a net actuator 24, and a net deployment and retrieval assembly 28 for transmitting motion between the net and its actuator 24. The net 20 comprises a net element 21 and a net loop 22 and a distal 25 and proximal 26 tie off suture that secures the net.

The device 10 can be used with any suitable or conventional endoscopic or laparascopic surgical equipment. For purposes oft his disclosure the device 10 is described in the context of use with an endoscope/colonoscope/sigmoidoscope type apparatus (not illustrated), of conventional or suitable construction. The scope is provided with an elongated body having a controllably flexible projecting end region. Surgical instruments, such as the device 10, may be introduced through an instrument channel, which extends through the scope body, for retrieving tissue targeted by the surgeon manipulating the scope.

The support unit 12 supports the net system 16 so that the net 20 can be inserted through the scope instrument channel by a surgeon. The support u nit 12 comprises a body 30 defining a passage and an elongated introducer 40 having a first end section 42 proximal and fixed with respect to the body 20 and a second end section 44 remote from the body. The introducer 40 is tubular and aligned with the body passage for receiving the net system.

The illustrated introducer 40 is a smooth, supple member capable of being snaked through the scope instrument channel into the subject and readily flexed into any shape required as the scope body is flexed by the surgeon. In the illustrated embodiment, the introducer 40 is a generally cylindrical, small diameter tube formed of non-reactive low friction plastic material, such as polytetrafluouroethylene. The first end section 42 is fixed to the body 30 while the second end section 44 houses the net for individual deployment and retrieval.

The net actuator 24 is adapted for reciprocating the deployment and retrieval assembly in the body and introducer to operate the net 20. The actuator 24 comprises a first handle 50 fixed with respect to the body 30 and a second handle 52 attached to the deployment and retrieval assembly 28 and movable with respect to the handle 50.

The second handle 52 is fixed to the assembly 28 and mounted on the handle 50 between its ends for longitudinal sliding movement. The second handle comprises a dual finger ring member 80 slidable on the handle 50. The handles 50, 52 as illustrated are formed from molded plastic materials.

The deployment and retrieval assembly 28 is constructed and arranged to transmit considerable deployment and retractive forces to the net while enabling the scope body to be freely manipulated and flexed to position the net where desired. The assembly 28 comprises a link comprises a first link section 70 and a second link section 71 connected to the actuator 24 for transmitting compressive and tensile forces between the handle 52 and a bore 58. The bore 58 is disposed within the center of the body 30. The link 70 transmits relatively substantial compressive forces without bending or breaking. The illustrated first link section 70 is formed from hypodermic needle stock, i.e., it is a cylindrical stainless steel tube. The second link section 71 as illustrated is a multi-strand cable. The first link section 70 joins the second link section 71 as the link exits the body 30.

The link 71 extends from the body 30 and within the introducer 40 so that it must flex with the introducer yet transmit compressive and tensile forces. The illustrated link 71 is closely surrounded by the body passage of the introducer passage 40. The link 71 is resiliently stiff compared to the supple introducer. When transmitting compressive forces, the link 71 is resiliently deformed to bow against the introducer wall. The link 71 has good compressive and tensile strength and is somewhat resiliently bendable. The link 71 will bend appreciably without yielding and kinking A first connector 80 and a second connector 82 fix the loop 22 in two locations with respect to the net 20. The proximal side of the net is tied off at a location 85 between the loop cables. As illustrated in FIG. 3, a tether 27 is used to tie off the proximal side of the net. This tether is shorter than conventional tethers that travel the full length of the introducer. No further tethering system is required, although additional net mounting techniques may be employed in the practice of the invention Referring now to FIG. 3, the first connector 80 joins the link 71 and the loop 22 together structurally. The illustrated connector 80 is a short tube crimped to both ends of the loop 22 and to the second link section 71. The illustrated connector tube is crimped about the loop and link to form a cross sectional shape, which is capable of rotating within the Introducer 40. The illustrated connector 80 is formed from hypodermic needle stock, like the first link section 70. The second connector 82 further joins opposing portions on the net loop 22 at a location proximal to the net 20 with respect to the first connector 80.

In the illustrated embodiment, the space between the two loop cables is utilized to fix the net element 21 with respect to the link 71. An intermediate region R, shown in FIG. 3, axially between the first connector 80 and the second connector 82 within the introducer 40 may be used. In an exemplary embodiment, the proximal side of the net element 21 with respect to the support system 12 is fixed to the net loops 22 at a convenient location 85. Suture material, or another known suitable method, may be used to tie the net to the loop.

The net 20 is deployed from the introducer second end 44 and manipulated by the surgeon to net severed tissue and secure the tissue for retrieval from the subject. The net 20 may be deployed after a snare or similar technique has severed the target tissue. The net 20 comprises a pouch-like net element 21 slidably supported on the loop 22.

The illustrated net loop 22 is formed from a loop of fine wire constructed and arranged to cooperate with the introducer to deploy and retract the net 20. The illustrated loop 22 is a stiff, resilient flexible wire having its respective ends crimped in place in two locations by the first and second connector 80, 82. When the net is deployed from the end of the introducer, the loop resiliently expands to a relaxed condition where the loop width is substantially greater than the introducer diameter. The deployed snare is guided to a position where it receives a target polyp or other tissue. The net is retracted by the surgeon. As the net is retracted into the introducer second end 44 the loop resiliently bears against the introducer wall so the loop resiliently collapses, narrowing the loop portion projecting from the introducer. Tissue or another object captured within the net element 21 is progressively constricted by the elastic nature of the net, allowing for a wide range of sized objects to fit inside the net without compromising the architecture preservation or the security of the object, as the net is being drawn toward the distal end of the introducer.

The net element 21 is an extremely light pouch-like structure having the net loop wire extending through the mesh about its periphery to form a net mouth slidably supported on the loop and a depending pouch. The net fibers are quite fine, yet sufficiently strong that the net element may slide along the loop wire in the direction away from the connectors 80, 82 to enclose tissue within the pouch as the net is retrieved and/or to gather the entire net at the distal net loop end when the net loop has been retrieved. The net has mini mal bulk so that when an empty net is retrieved, it easily moves completely into the introducer passage.

The illustrated net is formed from 100% nylon fibers having strand diameters of from about 0.0125 mm-0.04 mm. The fibers are woven in a diamond mesh pattern with the mesh strands spaced from 1 mm-3 mm and their intersections fixedly secured together. The illustrated netting material is substantially like that of a fine mesh hair net. The net is formed by cutting about a square, circular or elliptical section of the net, trimming or otherwise finishing the edges and threading the loop wire through the peripheral mesh elements. The cut net section size is selected sufficiently larger than the net loop area to assure that a pouch-like, tissue receiving portion suspends from the net mouth, but not too large to create undesirable bulk and difficulty packing the net when pulling it inside the shaft.

Attempting to fully retrieve a tissue containing net into the introducer 40 can result in tissue loss by forcing the tissue through the net. The net fibers are fine and strong so they may cut the tissue or they may be broken, either of which alternative is undesirable. A net actuator thumb ring may be provided with a tag (not illustrated) warning the surgeon not to continue retrieving the net against unusual resistance.

The present invention resolves problems faced by surgeons and nurses working with some prior art designs. Nurses and doctors have experienced difficulty in understanding the operation of the tether, specifically the interaction of the ring and post. Therefore, occasionally the device is operated incorrectly causing malfunction. The present design allows a nurse to pull back on the handle to conveniently pack the net inside the introducer passage.

Further, often a surgeon is required to manipulate the endoscope into difficult to access internal areas. Certain procedures require bending or twisting the endoscope. The area of the endoscope that is twisted or bent is called the articulation zone.

Some net devices have featured multiple connector designs in which the connectors are spaced somewhat adjacently with the second end section 44. In these designs, the multiple connectors on the net devices have resisted bending of the scope. Moreover, the friction created has made deployment of the net difficult once the scope has been desirably positioned by the surgeon. One advantage of the present invention is increased freedom of movement, and ease of net deployment, within the articulation zone.

During operation of the system 10, the surgeon experiences an increased ease of use over prior art designs. In the illustrated embodiment, the first connector 80 is axially disposed a distance from the second connector 82, such that only one connector is within the articulation zone (bounded by $A_1, A_2$), defined along the introducer 40 longitudinal axis, during deployment of the net element. In the illustrated system, the first connector 80 is disposed at least six inches from the second connector 82.

The articulation zone defines the axial portion of the introducer 40 within a substantially non-linear position. The articulation zone typically includes bends of greater than 30° and can exceed 200° at a radius of 0.75 inches or less.

Referring to FIG. 4, a portion of the system 10 is illustrated as positioned in a probable configuration within a subject. During operation of the scope, a surgeon may manipulate the second end section 44 of the introducer into a severe articulated position. At times, the second end section may be bent up to 180°, as illustrated in FIG. 4. Deployment of the net 20 in this and similar positions is difficult when the connectors 80, 82 are both within the articulation zone. The combined kinetic frictional force of each connector against the inside of the introducer passage would otherwise make deployment of the net difficult. As illustrated in FIG. 4, the surgeon more easily deploys the net in a variety of positions.

While two embodiments of the invention has been illustrated and described in considerable detail, the present invention is not to be considered limited to the precise constructions disclosed. Various adaptations, modifications and uses of the invention may occur to those skilled in the arts to which the invention relates. It is the intention to cover all such adaptations, modifications and uses falling within the scope or spirit of the annexed claims.

We claim:
1. An endoscopic surgical device comprising:
   a. a support unit including:
      i. a body having a first passage therethrough, and
      ii. an elongated introducer member having a first end section proximal and fixed with respect to said body and a second end section remote from the body, the introducer member having a second passage aligned with the first passage and opening at said second end section; and
   b. a tissue retrieving net system including:
      i. a net including a wire-like resilient loop and a net element having a mouth section slidably disposed on the loop and a tissue receiving pouch section, said loop terminating with two relatively parallel loop cables, said net disposed adjacent said second end section for deployment and retraction through said opening;
   c. said second passage having a diametrical extent smaller than a width of said loop as deployed, said introducer member engaging said loop at said opening and resiliently collapsing and elongated said loop as said net is retracted and moves into said second passage, said loop resiliently returning to its collapsed configuration as it is deployed;
   d. said net system further including a pair of connectors disposed on opposite sides of an articulation zone defined along the introducer longitudinal axis and positioned a distance from each other such that only one of the pair of connectors is movable into the articulation zone at a time, wherein at least one of the pair of connectors secures each loop cable; and
   e. wherein with respect to said support unit, a proximal portion of said net element directly contacts and is secured to the two relatively parallel loop cables.

2. The endoscopic surgical device of claim 1, wherein the proximal portion of said net element is secured to the two relatively parallel loop cables at a location adjacent a shoulder of one of the pair of connectors.

3. The endoscopic surgical device of claim 1, wherein the proximal portion of said net element is secured to the two relatively parallel loop cables at a location adjacent a proximal shoulder of one of the pair of connectors.

4. The endoscopic surgical device of claim 1, wherein the at least one of the pair of connectors holds the two relatively parallel loop cables together.

5. An endoscopic surgical device comprising:
   a. a support unit including:
      i. a body having a first passage therethrough, and
      ii. an elongated introducer member having a first end section proximal and fixed with respect to said body and a second end section remote from the body, the introducer member having a second passage aligned with the first passage and opening at said second end section; and
   b. a tissue retrieving net system including:
      i. a net including a wire-like resilient loop and a net element having a mouth section slidably disposed on the loop and a tissue receiving pouch section, said loop terminating with two relatively parallel loop cables, said net disposed adjacent said second end section for deployment and retraction through said opening; and
      ii. a net deployment and retrieval assembly extending through said first and second passages and connected to the net, said assembly including a motion transmitting member extending in said second passage to said loop;
   c. said second passage having a diametrical extent smaller than a width of said loop as deployed, said introducer member engaging said loop at said opening and resiliently collapsing and elongating said loop as said net is retracted and moves into said second passage, said loop resiliently returning to its uncollapsed configuration as it is deployed;
   d. said net system further including a first connector, a second connector, and an intermediate portion defined by an axial length of each of the two relatively parallel loop cables between the first connector and the second connector, wherein with respect to said support unit, proximal ends of the two relatively parallel loop cables are secured to a distal end of the motion transmitting member by the first connector, and distal ends of the two relatively parallel loop cables are secured to each other by the second connector; and
   e. wherein a proximal portion of said net element directly contacts and is secured to the two relatively parallel loop cables within the intermediate portion.

6. The endoscopic surgical device of claim 5, wherein the proximal portion of said net element is secured to the two relatively parallel loop cables at a location adjacent a shoulder of the second connector.

7. The endoscopic surgical device of claim 5, wherein the proximal portion of said net element is secured to the two relatively parallel loop cables at a location adjacent a proximal shoulder of the second connector.

8. The endoscopic surgical device of claim 5, wherein the second connector holds the two relatively parallel loop cables together.

9. The endoscopic surgical device of claim 5, wherein the first connector or second connector is movable about an articulation zone defined along the introducer longitudinal axis.

* * * * *